United States Patent
Funderburk

Patent Number: 5,456,940
Date of Patent: Oct. 10, 1995

[54] SYSTEM FOR LUBRICATING A SYRINGE BARREL

[75] Inventor: Jeffrey V. Funderburk, Granada Hills, Calif.

[73] Assignee: MiniMed Inc.

[21] Appl. No.: 219,074

[22] Filed: Mar. 28, 1994

[51] Int. Cl.⁶ ............ A61M 5/178; B05D 7/22; B05D 1/02
[52] U.S. Cl. ............ 427/2.1; 427/236; 427/421; 118/317; 118/500; 604/265
[58] Field of Search ............ 427/256, 421, 427/2.1, 230, 236, 479; 604/230, 265; 118/317, 500

[56] References Cited

U.S. PATENT DOCUMENTS

| | | | |
|---|---|---|---|
| 2,285,370 | 6/1942 | Staelin | 264/82 |
| 2,943,001 | 6/1960 | Socke | 117/96 |
| 3,247,004 | 4/1966 | Dosser | 427/104 |
| 3,455,728 | 7/1969 | Kiwiet | 427/236 |
| 4,767,414 | 8/1988 | Williams et al. | 604/230 |

FOREIGN PATENT DOCUMENTS 454630  2/1949  Canada.

Primary Examiner—Shrive Beck
Assistant Examiner—Fred J. Parker
Attorney, Agent, or Firm—Kelly Bauersfeld & Lowry

[57] ABSTRACT

A system and related method are provided for lubricating an interior surface of a device, such as the inner diameter surface of a syringe barrel. A fixture is provided for receiving and supporting the syringe barrel with an open rear end in alignment with a lubricant spray nozzle and an open front end in alignment with a counterflow air nozzle. Lubricant is sprayed via the lubricant spray nozzle into the syringe barrel in counterflow relation to an air flow discharged through the air nozzle, resulting in turbulent lubricant atomization and dispersal as a substantially uniform surface coating of interior surfaces of the syringe barrel.

18 Claims, 2 Drawing Sheets

SYSTEM FOR LUBRICATING A SYRINGE BARREL

BACKGROUND OF THE INVENTION

This invention relates generally to a system and method for applying a substantially uniform surface coating to an interior surface of a device, such as the inner diameter surface of a syringe barrel. More particularly, this invention relates to an improved system and method for lubricating the interior of a syringe barrel with a thin and substantially uniformly dispersed coating of a selected lubricant.

Medical syringes are widely used for containing and administering a selected medication to a patient. A typical syringe comprises a generally cylindrical syringe barrel having an open rear end for slide-fit reception of a piston plunger, and an open front or nose end which includes a luer fitting adapted for connection to a hypodermic needle, catheter tube, etc. Retraction of the piston plunger within the syringe barrel is effective to draw liquid such as medication or patient body fluid into the syringe barrel, whereas advancement of the piston plunger delivers liquid from the syringe barrel through the open front luer end thereof. Modern medical syringes of this general type are commonly manufactured predominantly from lightweight molded plastic suitable for disposal after a single use.

In many applications, it is desirable to prelubricate the inner diameter surface of the syringe barrel in order to reduce sliding friction forces as the piston plunger is advanced or retracted. Such reduction of friction forces is especially desirable in syringes designed for use in a programmable medication infusion pump having a battery operated and relatively low power drive means for displacing the piston plunger to administer medication to a patient. Examples of such medication infusion pumps include those available from MiniMed Technologies of Sylmar, Calif. under Model Nos. 504 and 506. See also U.S. Pat. Nos. 4,562,751; 4,678,408, and 4,685,903.

In the past, syringe barrel lubrication has been accomplished by manually placing one or more drops of a selected nontoxic lubricant in liquid form into open rear end of the syringe barrel, and thereafter inserting and stroking the piston plunger with a twisting motion to distribute the lubricant over the inner diameter surface of the barrel. This technique, however, is manual labor intensive and inherently results in at least some scrubbing contact between a piston plunger seal and dry barrel surfaces prior to significant distribution of the lubricant. This scrubbing piston seal-barrel contact often results in chafing of the seal material or rubbing off of prelubricated or preconditioned seal surface treatment onto dry barrel surfaces, thereby reducing the intended effect of such seal surface treatments.

Alternative attempts to lubricate a syringe barrel have involved spraying a liquid-based barrel lubricant into the open rear end of the syringe barrel prior to assembly with the syringe plunger. These attempts have unfortunately resulted in substantially nonuniform application of the barrel lubricant, typically with the lubricant concentrated within the forward or luer end region of the barrel. Subsequent assembly of the syringe plunger with the barrel has still resulted in nonuniform lubrication dispersal and/or rubbing of seal surface treatments onto dry barrel surfaces at the open rear end of the syringe barrel upon initial contact with the piston plunger.

There exists, therefore, a significant need for improvements in apparatus and method for lubricating internal surfaces of a syringe barrel or similar device, particularly wherein a substantially uniform surface coating of lubricant is applied to the syringe barrel prior to barrel assembly with a piston plunger. The present invention fulfills these needs and provides further related advantages.

SUMMARY OF THE INVENTION

In accordance with the invention, an improved system and method are provided for spray application of a substantially uniform surface coating of a lubricant or the like onto an inner surface of a device, such as the inner diameter surface of a syringe barrel. The system comprises a fixture for receiving and supporting a syringe barrel with an open rear end and an open front or luer end in respective alignment with a lubricant spray nozzle and a counterflow air nozzle. Lubricant and air are sprayed simultaneously from opposite directions into the barrel interior, resulting in turbulent lubricant atomization and dispersal as a finely divided mist for substantially uniform surface coating of the inner diameter surface of the syringe barrel.

In the preferred form, the fixture receives and supports a syringe barrel in a vertical orientation, in substantial coaxial vertical alignment with the lubricant spray and counterflow air nozzles. The lubricant spray nozzle delivers an upwardly projected and substantially atomized lubricant spray into the open rear end of the syringe barrel. At the same time, the air nozzle delivers a downwardly directed counterflow air spray via the narrow open luer end of the syringe barrel into the barrel interior. A resultant counterflow action within the syringe barrel results in turbulent lubricant dispersal as a substantially uniform atomized layer applied to the inner diameter surface of the syringe barrel. The thus-lubricated syringe barrel can be removed from the fixture for subsequent assembly with a piston plunger.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
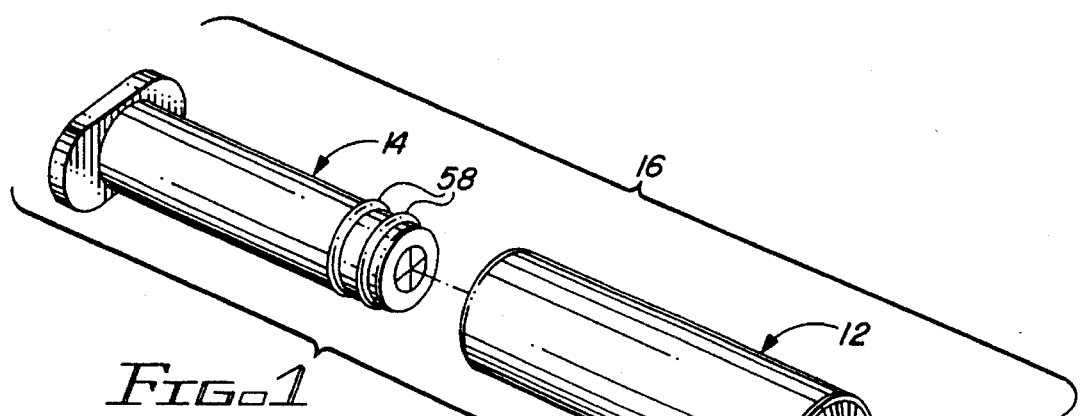
FIG. 1 is an exploded perspective view illustrating a medical syringe including a hollow syringe barrel for assembly with a piston plunger.
Figure 2:
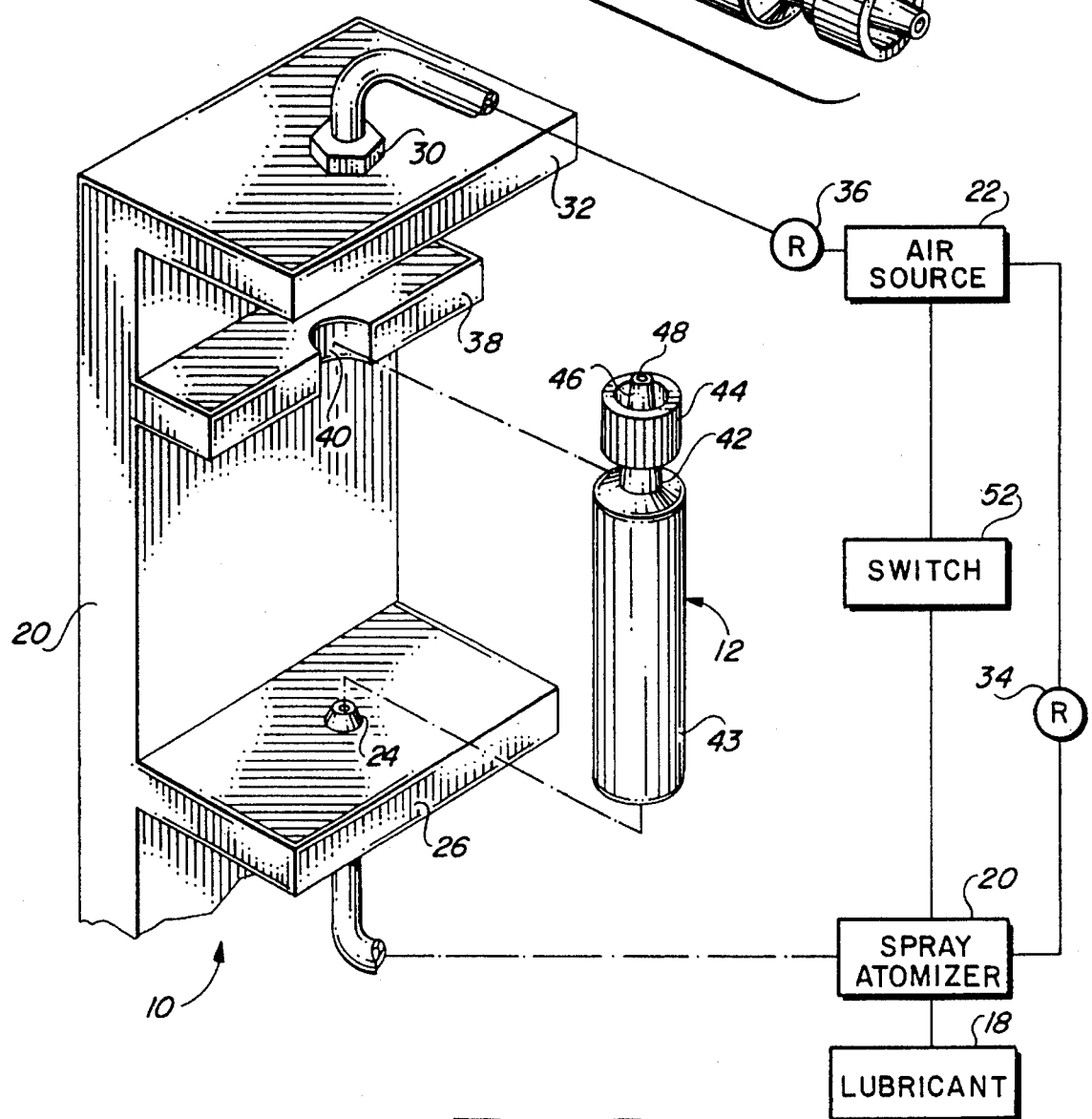
FIG. 2 is an exploded fragmented perspective view, shown partially in schematic form, illustrating a lubricant fixture for receiving and supporting a syringe barrel.

As shown in the exemplary drawings, a lubricant system referred to generally in FIG. 2 by the reference numeral 10 and related method are provided for lubricating an interior surface of a device, particularly such as the inner diameter surface of a syringe barrel 12. The lubricated syringe barrel is subsequently assembled with a piston plunger 14 (FIG. 1) to form a syringe 16 for use in medical applications and the like.

The improved system 10 and related method of the present invention are designed to coat internal surfaces of the syringe barrel 12 with a substantially uniform and thin layer coating of a selected lubricant 18, such as a liquid silicone-based lubricant of a type commonly used for lubrication of medical syringes. The system 10 includes a spray atomizer 20 for spraying the lubricant into the syringe barrel 12, in counterflow relation to an air flow stream. The counterflow action results in turbulent atomization of the sprayed lubricant to coat the internal surfaces of the syringe barrel with a finely atomized or misted coating which is substantially uniformly dispersed.

FIG. 2 illustrates the lubrication system 10 including the spray atomizer 20 supplied with the lubricant 18 from a suitable supply or reservoir, in parallel relation to a source of pressurized air 22. While the spray atomizer 20 may take various forms, a preferred unit is available from Ivek Corporation of North Springfield, Vt. under the model designation Digispense 7. This spray atomizer 20 includes a pump and pump controller for delivering an output to a lubricant spray nozzle 24 supported on a lower platform 26 of a fixture 28. The spray nozzle 24 is aimed upwardly and is constructed to provide a finely atomized spray of the silicone-based lubricant, with a preferred nozzle construction available from Ivek Corporation under the name Sonicair Atomizing Nozzle.

The pressurized air source 22 is also connected to an upper counterflow air nozzle 30 mounted on an upper platform 32 of the fixture 28. Suitable pressure regulators 34 and 36 may be provided for regulating the pressure of air supplied to the spray atomizer 20 and counterflow air nozzle 30, respectively. Importantly the counterflow air nozzle 30 is aimed downwardly from the platform 32, in substantial vertical alignment with the underlying spray nozzle 24 on the lower platform 26.

A syringe support wall 38 is carried by the fixture 28 in a predetermined position disposed vertically between the lower and upper platforms 26 and 32. As shown, the support wall 38 includes a forwardly or laterally open, generally half-cylindrical recess 40 having a size and shape for close slide-fit reception of a narrow cylindrical neck 42 of the syringe barrel 12. In this regard, the syringe barrel 12 shown in the illustrative drawings has a typical construction to include a generally cylindrical barrel body 43 joined by the neck 42 of smaller cross sectional diameter with a luer fitting 44 adapted for connection to a hypodermic needle, catheter tube, etc. The luer fitting 44 surrounds a forward or luer end 46 within which a relatively small open port 48 is formed therein. The rear end of the syringe barrel 12 defines a comparatively larger opening 50 (FIG. 3) for slide-fit reception of the piston plunger 14, as viewed in FIG. 1.

Figure 3:
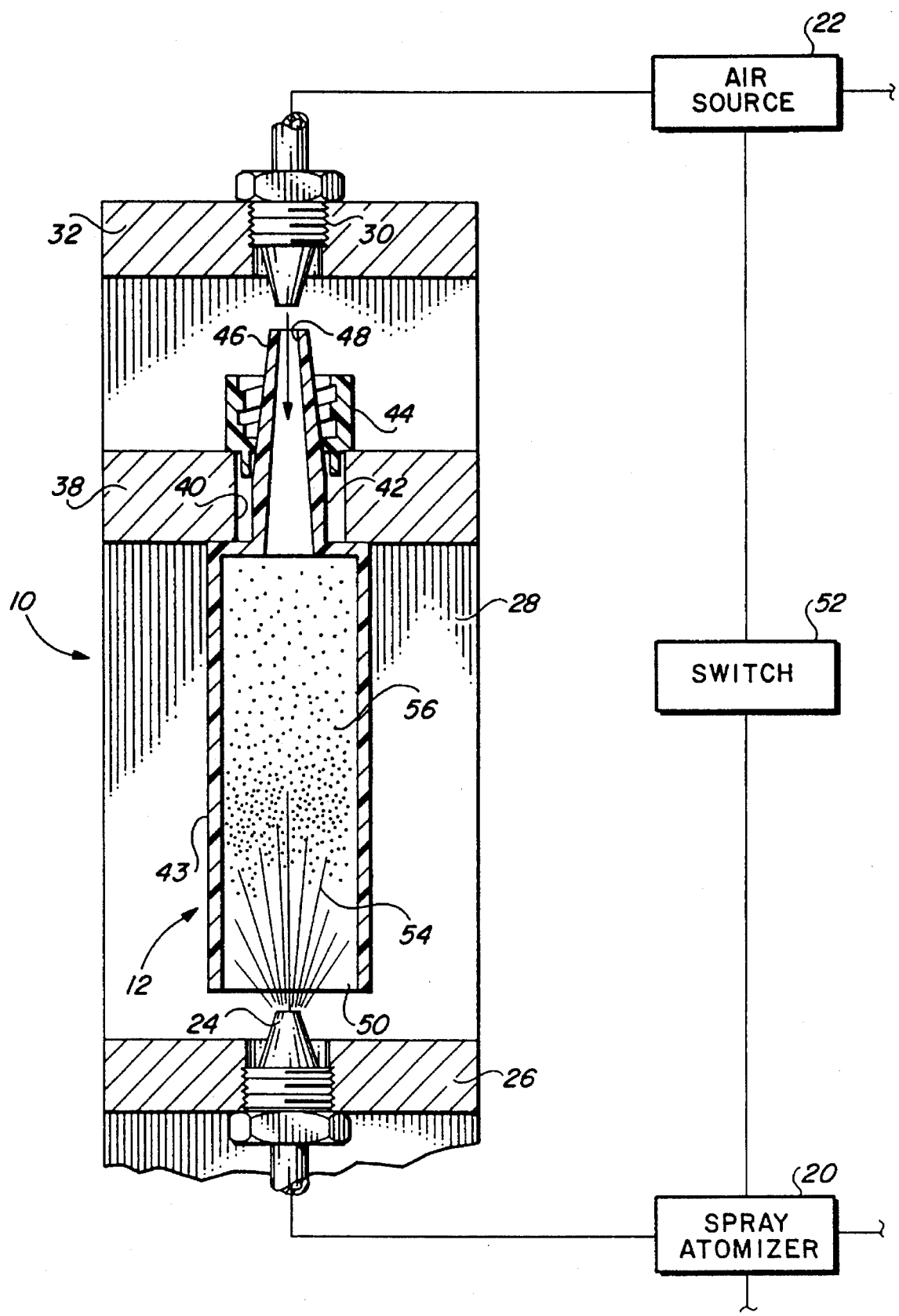
FIG. 3 is an enlarged fragmented vertical sectional view, shown partially in schematic form, illustrating spray lubrication of the inner diameter surface of the syringe barrel.

When the syringe barrel 12 is seated on the fixture, with the neck 42 received within the support wall recess 40, the syringe barrel is positioned in aligned, slightly spaced relation with the lower lubricant spray nozzle 24 and the upper counterflow air nozzle 30. That is, as shown in FIG. 3, the open rear end 50 of the syringe barrel 12 is positioned directly over the lubricant spray nozzle 24. Similarly, the open port 48 at the luer end 46 is aligned with the downwardly aimed counterflow air nozzle 30 on the upper platform 32.

With the syringe barrel 12 mounted on the fixture, as described, the spray atomizer 20 is activated, such as by operation of an appropriate push-button or foot-operated switch 52. At the same time, the air source 22 is connected to the counterflow air nozzle 30. Thus, simultaneously, the spray atomizer 20 delivers an upwardly directed lubricant spray 54 (FIG. 3) into the interior of the syringe barrel, while a downwardly directed counterflow stream of air is provided through the nose port 48 into the barrel interior. The counterflow action of these two fluid streams causes a turbulent misted dispersion of the atomized lubricant spray, such that the lubricant is applied as a fine, substantially atomized and a thin surface coating 56 with substantially uniform coverage of interior barrel surfaces. By contrast, uneven distribution of the lubricant, particularly by collection of excess lubricant at the luer end 46 of the syringe barrel, is avoided.

The thus-lubricated syringe barrel 12 can then be assembled with the syringe plunger 14, to form the completed assembled syringe 16. Seal structures 58 on the syringe plunger 14, such as the illustrative pair of elastomer O-ring seals, thus engage the lubricated interior surfaces of the syringe barrel 12, when the syringe is finally assembled. The O-ring seals 58 do not contact or scrub with dry, unlubricated surfaces within the syringe barrel.

A variety of further modifications and improvements to the syringe lubrication system and method of the present invention will be apparent to those skilled in the art. For example, it will be understood that the flow rates and pressures applicable to the opposed lubricant and air spray nozzles 24 and 30 may be adjusted as needed in accordance with the size and shape of the specific syringe barrel to achieve substantially uniform misted lubricant coverage of interior surfaces of the barrel body 43. Accordingly, no limitation on the invention is intended by way of the foregoing description and accompanying drawings, except as set forth in the appended claims.

What is claimed is:

1. A system for lubricating interior surfaces of a syringe barrel having an open rear end and an open front end, said system comprising:

a fixture for receiving and supporting a syringe barrel;

first spray means for delivering a lubricant spray into the open rear end of the syringe barrel supported by said fixture; and second spray means for delivering a counterflow spray into the syringe barrel through the open front end thereof, in opposition to the lubricant spray, to result in turbulent dispersal of the lubricant spray within the syringe barrel so that interior barrel surfaces are coated with a substantially uniform surface coating of lubricant.

2. The system of claim 1 wherein said fixture supports the syringe barrel in a generally vertical orientation with the open front end thereof presented in an upward direction.

3. The system of claim 1 wherein said first and second spray means include a pair of spray nozzles mounted on said fixture in opposed, generally coaxially aligned relation.

4. The system of claim 3 wherein said fixture supports the syringe barrel with the open rear and front ends thereof and an open end of narrower diameter than said rear end, said mounting step including said first and second spray nozzles, respectively.

5. The system of claim 1 wherein said second spray means delivers a counterflow air spray through the open front end of the syringe barrel.

6. The system of claim 1 wherein said first spray means delivers a liquid-based lubricant spray into the syringe barrel.

7. The system of claim 1 further including control means for simultaneously operating said first and second spray means.

8. The system of claim 1 wherein the syringe barrel comprises a generally cylindrical barrel body defining said open rear end and having a forward end connected by a neck of reduced cross sectional size to said open front end, and wherein said fixture includes a support wall defining a laterally open recess for seated reception of the neck of the syringe barrel.

9. A system for lubricating interior surfaces of a hollow device having opposite open ends, said system comprising:

a fixture for receiving and supporting the device;

first spray means for delivering a lubricant spray into one end of the device; and second spray means for delivering a counterflow spray into the opposite end of the device, in opposition to the lubricant spray, to result in turbulent dispersal of the lubricant spray so that interior surfaces of the device are coated with a substantially uniform surface coating of lubricant.

10. The system of claim 9 wherein the lubricant spray is a liquid lubricant, and wherein the counterflow spray is air.

11. The system of claim 9 wherein said wherein said first and second spray means include a pair of spray nozzles mounted on said fixture in opposed, generally coaxially aligned relation.

12. The system of claim 11 wherein said fixture supports the device in a generally vertical orientation positioned between, and aligned with, said first and second spray nozzles, respectively.

13. The system of claim 9 further including control means for simultaneously operating said first and second spray means.

14. A method of lubricating interior surfaces of a device having opposite open ends, said method comprising the steps of:

spraying a lubricant spray into one end of the device; and spraying a counterflow spray into the opposite end of the device, in opposition to the lubricant spray, to result in turbulent dispersal of the lubricant spray so that interior surfaces of the device are coated with a substantially uniform surface coating of lubricant.

15. The method of claim 14 wherein said lubricant spraying step comprise spraying a liquid lubricant into the device, and wherein said counterflow spraying step comprises spraying a counterflow air flow into the device.

16. The method of claim 15 including the step of mounting the device on a fixture in a vertical orientation.

17. The method of claim 16 wherein said lubricant spraying step comprises spraying the lubricant upwardly into the device, and wherein said counterflow spraying step comprises spraying the counterflow spray downwardly into the device.

18. The method of claim 17 wherein the device is a syringe barrel having an open rear end and an open end of narrower diameter than said rear end, said mounting step including mounting the syringe barrel on the fixture in a vertical orientation with the front end presented upwardly.

* * * * *